United States Patent [19]

Gajjar et al.

[11] Patent Number: 4,891,629

[45] Date of Patent: Jan. 2, 1990

[54] BINARY GAS ANALYZER INSTRUMENT AND ANALYSIS METHOD

[75] Inventors: Jagdish T. Gajjar, Clifton Park; Edwin C. Underkoffler; Craig A. Wroblewski, both of Schenectady; Michael F. Roman, Rotterdam, all of N.Y.

[73] Assignee: General Electric Company, Schenectady, N.Y.

[21] Appl. No.: 194,635

[22] Filed: May 16, 1988

[51] Int. Cl.⁴ ............................................. G01N 27/18
[52] U.S. Cl. ..................................... 340/632; 73/27 R; 73/25
[58] Field of Search ...................... 73/25, 26, 27 R, 23; 422/90, 95, 96; 340/632

[56] References Cited

U.S. PATENT DOCUMENTS

| | | | |
|---|---|---|---|
| 2,326,884 | 8/1943 | Phelps | 73/27 R |
| 2,591,762 | 4/1952 | Zaikowsky | 73/27 R |
| 3,680,359 | 8/1972 | Lynch | 73/27 R |
| 3,895,630 | 7/1975 | Bachman | 73/27 R |
| 3,961,900 | 6/1976 | Gintelia et al. | 340/632 |
| 4,328,780 | 5/1982 | Andrew | 73/27 R |
| 4,476,096 | 10/1984 | Hoht | 422/96 |

FOREIGN PATENT DOCUMENTS

| | | | |
|---|---|---|---|
| 594696 | 3/1934 | Fed. Rep. of Germany | 73/27 R |
| 1387412 | 3/1975 | United Kingdom | 422/95 |
| 2091882 | 8/1982 | United Kingdom | 73/27 R |

*Primary Examiner*—Hezron E. Williams
*Attorney, Agent, or Firm*—Jerome C. Squillaro

[57] ABSTRACT

A binary gas analyzer instrument and analysis method for determining percent composition of a cooling gas within a turbine generator is disclosed. The instrument includes a measurement block having a plurality of cells therein, some of which comprise sealed cells containing a known reference gas. One of the cells comprises a measurement cell and contains the binary gas mixture to be evaluated. Each of the cells contains a thermistor and a heater is provided for keeping the cells at a substantially constant temperature. An electric current supply provides a constant current to each thermistor for self-heating, and the gas within each cell conducts heat away from the thermistor at a distinctive rate. Measuring apparatus is selectably connectable across each cell thermistor to measure the voltage drop across said thermistors, and computational apparatus is provided to automatically translate the measured voltage drop across the measurement cell thermistor into a percent compositional reading of the binary gas constituents. Translation is accomplished by the computational apparatus with reference to the voltage drop across at least one of the reference cell thermistors.

45 Claims, 7 Drawing Sheets

BINARY GAS ANALYZER INSTRUMENT AND ANALYSIS METHOD

BACKGROUND OF THE INVENTION

1. Technical Field

This invention relates in general to percent compositional analysis of a binary gas mixture, and more particularly, to a binary gas analyzer instrument and analysis method effective to indicate percent contamination of a cooling gas within a turbine generator.

2. Description of Prior Art

For many years, all large steam turbine driven electrical generators (turbo generators) have been designed to capitalize on the improved cooling capabilities of hydrogen, contrasted with air. Hydrogen gas has been found to be an excellent cooling medium, however, it is not without problems. Air is usually an ever present and potential contaminant, and due to the combustible nature of a hydrogen-oxygen mixture, precaution must be taken to prevent its existence at dangerous levels. High-purity hydrogen will not support combustion, and as long as the purity is above 95% there is no danger of explosion.

Conversely, if the percent air concentration in a hydrogen-air mixture exceeds 15% by volume, the mixture is potentially explosive. Thus, it is important that in operating hydrogen gas cooled generators, the relative composition of contaminant air in the hydrogen cooling gas be continually monitored.

The maximum risk of an explosive mixture developing occurs when the generator is out of service, particularly during time of purging or refilling, and when various types of maintenance or repair activities are underway. In order to lessen the possibility of an explosive mixture developing, it is standard practice in filling the generator for air to first be displaced from the generator by carbon dioxide ($CO_2$), and then for $CO_2$ to be displaced by filling with hydrogen ($H_2$). Purging of the generator entails the reverse process.

The principle prior art means for monitoring air contamination within a gas cooled generator was developed by the assignee of the present invention several decades ago. This monitoring means consists of a Golay cell and a reference cell mounted in a brass housing together with a power unit, a flowrator, a wheatstone bridge circuit, and an indicating meter. Two arms of the bridge consist of a filament each and the other two consist of bridge completion resistors of comparable resistance value. One of the filaments is enclosed in the reference cavity of the detector in sealed air, while the other is placed in the measuring cell having the mixture to be measured. Imbalances in thermal conductivity between the two cells, as measured by imbalances in the resistances of the two filaments, are indicated by the bridge imbalance current and serve as the measure of the composition of the mixture. Although the instrument offers a reasonable indication of the composition of the binary mixtures used, it does have several shortcomings. For example, this prior art instrument is very sensitive to variations in supply voltage and to the temperature of the detector block. Further, for air and $CO_2$ in hydrogen detection, the accuracy and sensitivity are relatively poor in the critical 0% to 20% contamination region, and the instrument requires manual calibration during each use.

Another prior art monitoring system is disclosed in U.S. Pat. No. 4,440,017, also owned by the same assignee as the present invention. This patent describes a dual, water and hydrogen gas cooling system for an electrical generator and a device for monitoring leakage of hydrogen gas into the water cooling system, but not gas contamination of the hydrogen gas.

During the years of prior art monitoring methods of hydrogen cooled turbo generators, there have been occassional cases in which internal explosions have occured. Therefore, there is a genuine need for an improved gas mixture monitoring system to assist an operator in safely performing the normal functions of filling, purging and operating gas cooled turbine driven generators.

SUMMARY OF THE INVENTION

As more fully described herein, the present invention comprises a gas analyzer instrument and analysis method capable of determining the percent composition of a gas mixture composed of two known constituents. The analyzer instrument includes a first reference cell having a first gas therein with a thermal conductivity near the thermal conductivity of one of the known constituent gases, and a measurement cell containing the binary gas mixture to be analyzed. A thermistor is positioned within each of the cells and maintaining means is provided for maintaining the cells at a substantially constant temperature. The instrument also includes electric current supply means for providing a constant current to each of the thermistors for self heating, with the gas in each of the cells conducting heat away from the thermistor therein, and voltage measuring means selectably connectable across each of the thermistors for measuring the voltage drop across the thermistors. Lastly, computational means provides for automatic translation of the measured voltage drop across the measurement cell thermistor into a percent compositional reading of the binary gas constituents. Translation is accomplished by the computational means with reference to the voltage drop across the first reference cell thermistor.

In a further embodiment, the analyzer instrument is capable of determining the percent composition of the constituents within each of a plurality of different binary gas mixtures. This embodiment includes a second reference cell which has a second gas therein with a thermal conductivity near the thermal conductivity of one of the constituent gases of the plurality of different binary gas mixtures. The computational means translates the voltage drop across the measurement cell thermistor into a percent compositional reading of the constitutents for a particular binary gas mixture utilizing the voltage drop across at least one of the first and second cell thermistors as a reference.

In another aspect, the invention comprises an analysis method for determining the percent composition of a binary gas mixture of known constituents which includes the steps of: providing a first reference cell and a second reference cell, each cell having a thermistor therein, said cells also having a first gas and a second gas sealed therein, respectively, the first gas having a thermal conductivity near the thermal conductivity of one of the two constituent gases and the second gas having a thermal conductivity near the thermal conductivity of the other of the two constituent gases; providing a measurement cell with a thermistor therein; introducing the binary gas mixture into the measurement cell; maintaining the cells at a substantially constant temperature;

supplying a substantially constant electric current to each of the thermistors for heating thereof, the gas in each of said cells conducting heat away from the thermistor therein; measuring the voltage drop across each of the thermistors; and correlating the voltage drop across the measurement cell thermistor with a percent compositional reading of the binary gas mixture constituents, said correlating step utilizing the voltage drop across at least one of the first and second cell thermistors as a reference.

Accordingly, a principle object of the present invention is to provide an improved analyzer instrument and analysis method capable of being used to determine the percent composition of a gas mixture composed of two known constituents.

Another object of the present invention is to provide an improved analyzer instrument and analysis method capable of being used to determine the percent composition of the constituents within each of a plurality of different known binary gas mixtures.

A further object of the present invention is to provide such an instrument and method which is capable of safely monitoring operation of a hydrogen gas cooled turbo generator.

A yet further object of the present invention is to provide such an instrument and method which is capable of accurately determining the percent composition of a binary gas mixture within a turbo generator.

But another object of the present invention is to provide such an instrument and method which requires no manual adjustment while monitoring operation of a hydrogen gas cooled turbo generator.

BRIEF DESCRIPTION OF THE DRAWINGS

These and other objects, advantages and features of the present invention will be more readily understood from the following detailed description when considered in conjunction with the accomanying drawings in which.

DETAILED DESCRIPTION OF INVENTION

Figure 1:
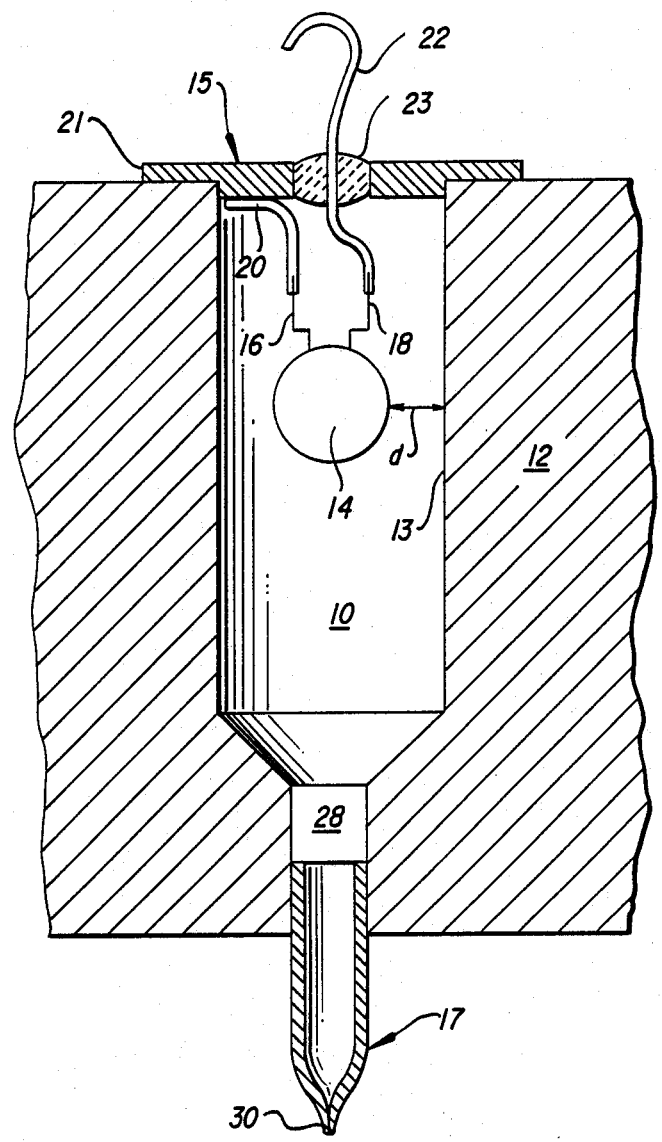
FIG. 1 is a cross-sectional view of one embodiment of the basic heat conductivity cell of the present invention.

In general, the novel apparatus and method of this invention, as defined by the appended claims, utilizes two basic principals, namely: (1) different gases have different thermal conductivities, and (2) thermistors positioned within gas filled chambers and supplied with constant current stabilize at different voltages which depend upon the heat conductivity of the respective surrounding gases. A detailed description of one invention embodiment incorporating these principals is provided herein with reference its use in the turbo power generation field. However, those skilled in the art will readily appreciate that many other uses of the invention are possible. The appended claims are intended to encompass all such uses.

As noted initially, operation of a hydrogen gas cooled turbine driven electrical generator typically requires compositional percent information for three different, known binary gas mixtures, i.e., air and carbon dioxide ($CO_2$), $CO_2$ and hydrogen, and air and hydrogen. These mixtures occur at different times during the filling, operation and purging of the turbo generator. Attention to percent contamination of air in hydrogen is particularly important because of its explosive nature at certain critical levels. Constant monitoring is required since air contamination within the generator is a consistent problem resulting from the tendency of pressurized hydrogen gas to leak from the generator.

Since percent composition of the air and $CO_2$ mixture and the $CO_2$ and hydrogen mixture are less important (because the presence of $CO_2$ is merely temporary and neither mixture is potentially explosive), the embodiment described herein contains only two reference cells in addition to the measurement cell. Such a cell configuration allows for the calculation of percent composition of each of said three mixtures within an acceptable range of error for each mixture. If desired, however, instrument accuracy can be improved by having reference gases at each end of each measurement range, i.e., by having reference gases which comprise the constituent gases of each binary mixture to be evaluated. Alternatively, if accuracy is less important, the invention can be implemented with only one reference cell having a gas sealed therein which comprises a constituent gas of the binary mixture to be evaluated, or has a thermal conductivity near that of a constituent gas.

Since percent composition of the hydrogen-air mixture is critical, a first reference cell has a first gas sealed therein with a thermal conductivity near either that of air or hydrogen gas, and the second reference cell has a second gas sealed therein with a thermal conductivity near the thermal conductivity of the other of said two constituent gases. Although the cells are maintained at a substantially constant temperature, measurements across the sealed reference cells allow compensation for any temperature drift, which is important since the voltage readings across the thermistors depend greatly upon the temperature of the cells (see FIG. 6) and failure to compensate for even slight temperature variations would effect instrument accuracy.

Preferably, the first reference gas comprises nitrogen, since nitrogen gas is known to closely approximate the thermal conductivity of air and is more readily available in bottled form, and the second reference gas comprises heluim, which is inert and is known to closely approximate the thermal conductivity of hydrogen, which has a much greater tendency to leak from a sealed container.

As the thermistors undergo a heating effect from the flow of a constant current therethrough, heat is conducted by the constrained gases radially outwards until the temperature of each thermistor stabilizes. The respective stabilization temperatures are dependent upon the thermal conductivity of the gas sealed within each cell, and at equilibrium, the voltage measured across each cell thermistor provides an indication of thermal conductivity of the gas constrained therein. Provision of a constant current to the thermistors is important to eliminate error which would otherwise be introduced due to current changes causing self-heating changes within the thermistors.

It is assumed in the discussion below that at each stage of the turbo generator operating process, an operator is aware of the constituent gases comprising a particular mixture under evaluation. For example, during normal system operation, the analyzer instrument is manually set to indicate that the mixture under analysis comprises % hydrogen in air, with 99% being a typical operating percentage.

Referring now to FIG. 1, a cross-sectional view of one embodiment of the basic cell or cavity 10 of the invention is illustrated. Cell 10 comprises a cylindrical bore within a block 12, preferably manufactured of brass. As shown, cell 10 is a sealed reference cell, with one end closed by a hermetic seal 15 and the other end by a sealed fill tube 17.

Within cell 10 is a thermistor 14 radially suspended by very fine electric leads 16 and 18. Fine leads 16 and 18 are electrically connected to leads 20 and 22, respectively, and are utilized to minimize thermal conduction through the wires from thermistor 14. Hermetic seal 15 is a commercially available item which includes a disk-shaped, metallic rim 21 and a central, electrically isolating glass portion 23. Seal 15 is soldered airtight to block 12. Lead 20 is electrically grounded to block 12, via metallic rim 21, and lead 22 is electrically isolated from block 12 by glass seal 23.

Cell 10 can be constructed of various shapes as desired, such as cylindrical, spherical or cubical, however, the distance "d" from thermistor 14 to wall 13 of cell 10 is important. This is because as distance "d" increases, net thermal conductivity of the gas filled chamber decreases, which means the resulting stabilization temperature rises, thereby making it more difficult to measure differences in voltage drop across the thermistors.

As noted, cell 10 is sealed at its bottom end by a closed fill tube 17. Fill tube 17 consists of standard copper tubing which resides within a bore 28 at the bottom of cell 10. Filling of cell 10 with a reference gas entails evacuating the cell through tube 17 and then filling with the reference gas. Cell 10 may be purged several times in this manner and then filled under slight pressure with the reference gas. Once cell 10 is filled, tube 17 is pinched closed at 30 to form an airtight seal.

Although the invention can be configured to utilize positive temperature coefficient (PTC) thermistors, negative temperature coefficient (NTC) of resistivity thermistors are believed preferable. This is because a constant current source connected across PTC thermistors presents the possibility of runaway since PTC thermistors experience increasing resistance with increasing temperature.

Various negative temperature coefficient thermistors of different size and accuracy can be utilized in the invention. By way of nonlimiting example, thermistor 14 comprises a roughly one-tenth of an inch diameter glass ceramic NTC thermistor such as that manufactured by Yellow Springs Instrument Company, Industrial Division, Yellow Springs, Ohio and marketed as model number YSI 46033.

Figure 2:
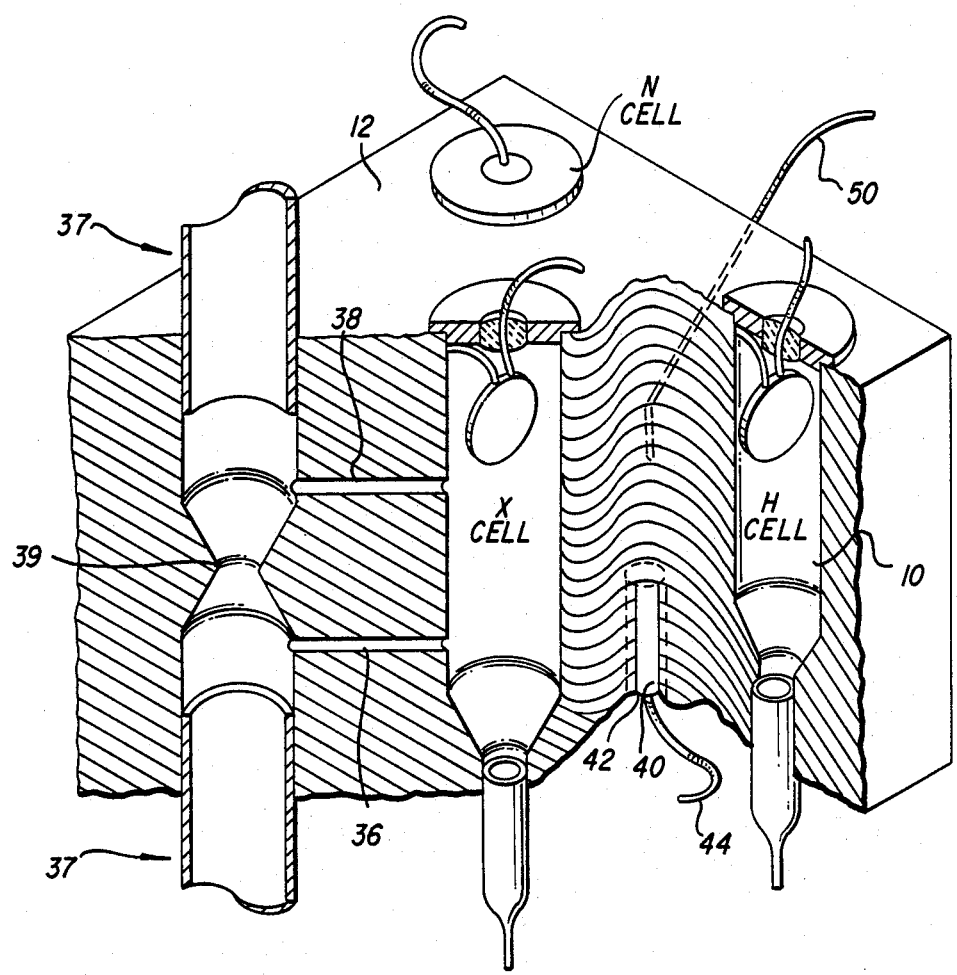
FIG. 2 is a partially cutaway perspective view of a measurement cell block containing a plurality of heat conductivity cells of the embodiment of FIG. 1.

As shown in FIG. 2, the generator monitoring embodiment of the invention includes a helium reference cell, labeled "H CELL", a nitrogen reference cell, labeled "N CELL" and a measurement cell, labeled "X CELL". Each cell is substantially identical, however, X CELL contains an inlet orifice 36 and an outlet orifice 38 for the introduction and removal of binary gas mixtures via a piping system 37. A constriction 39 in piping 37 within block 12 between inlet orifice 36 and outlet orifice 38 results in shunting of the binary gas mixture to the X CELL. Gas is carefully discharged from piping 37 to the atmosphere through vents in the roof of the power station (not shown).

Cells 10 are defined by cylindrical drill holes in block 12. As one detailed example, block 12 comprises a 2 inch cube of brass and each cell is substantially 5/16th of an inch in diameter and 1¼ inch in depth. Construction of block 12 from brass beneficially results in ready dissipation of any excess heat above the desired constant temperature. As shown, X CELL, H CELL and N CELL are positioned in a triangular-shaped configuration within block 12. This configuration allows the introduction of a heat source 40 substantially central the cells for even heating thereof. Heat source 40 is located within a bore 42 in the bottom of block 12. An electric lead 44 extends from heat source 40 and connects source 40 to a constant temperature control (see FIG. 3). Lead 50 is to a temperature sensor (not shown) embedded within block 12 approximately central the cells. The temperature sensor provides feedback information to the constant temperature control.

When in operation, block 12 is maintained at a substantially constant temperature, which is preferably approximately 50 degrees Celsius. However, there is clearly an acceptable range about this temperature within which the analyzer instrument and analysis method will operate satisfactorily. The low end of the range is defined by the preference that block 12 be maintained at a temperature above the hottest expectant ambient temperature of the room within which the instrument is located, otherwise temperature control could be lost, i.e., unless expensive cooling apparatus is introduced. The upper end of the acceptable range is defined by the need for an adequate differential between the temperature of the thermistors when at equilibrium and the constant temperature of block 12 so that heat will be measurably (i.e., via the voltage drop across each thermistor) conducted away from the thermistors by the constrained gases.

During normal operation, the invention contemplates the continuous sampling of cooling gases from the turbo generator via piping 37 for analysis. As discussed below, percent composition readings (i.e., % hydrogen in air) are preferably periodically calculated for the gas mixture constrained within X CELL. For example, updated readings can be calculated approximately every second. However, there is one consideration to note. With such a continuous flow sampling device the binary gas mixture introduced through inlet orifice 36 into X CELL and removed therefrom through outlet orifice 38, must be constrained within X CELL for a sufficient length of time to stabilize at a substantially constant temperature, otherwise an error is introduced into the calculations due to the temperature difference of the incoming gas and the block stabilization temperature. In addition, the X CELL thermistor should be positioned above the outlet orifice 38 to avoid an error which otherwise introduced by flow of the binary gas mixture about the thermistor, which is why, e.g., gas is preferably shunted to the X CELL from piping 37 rather than the X CELL being defined within piping 37.

If desired, block 12 can be located a substantial distance from the monitored turbo generator, such as 100 feet or further away; however, close positioning is believed preferable to enhance instrument response time to a changing percent composition within the generator.

Figure 3:
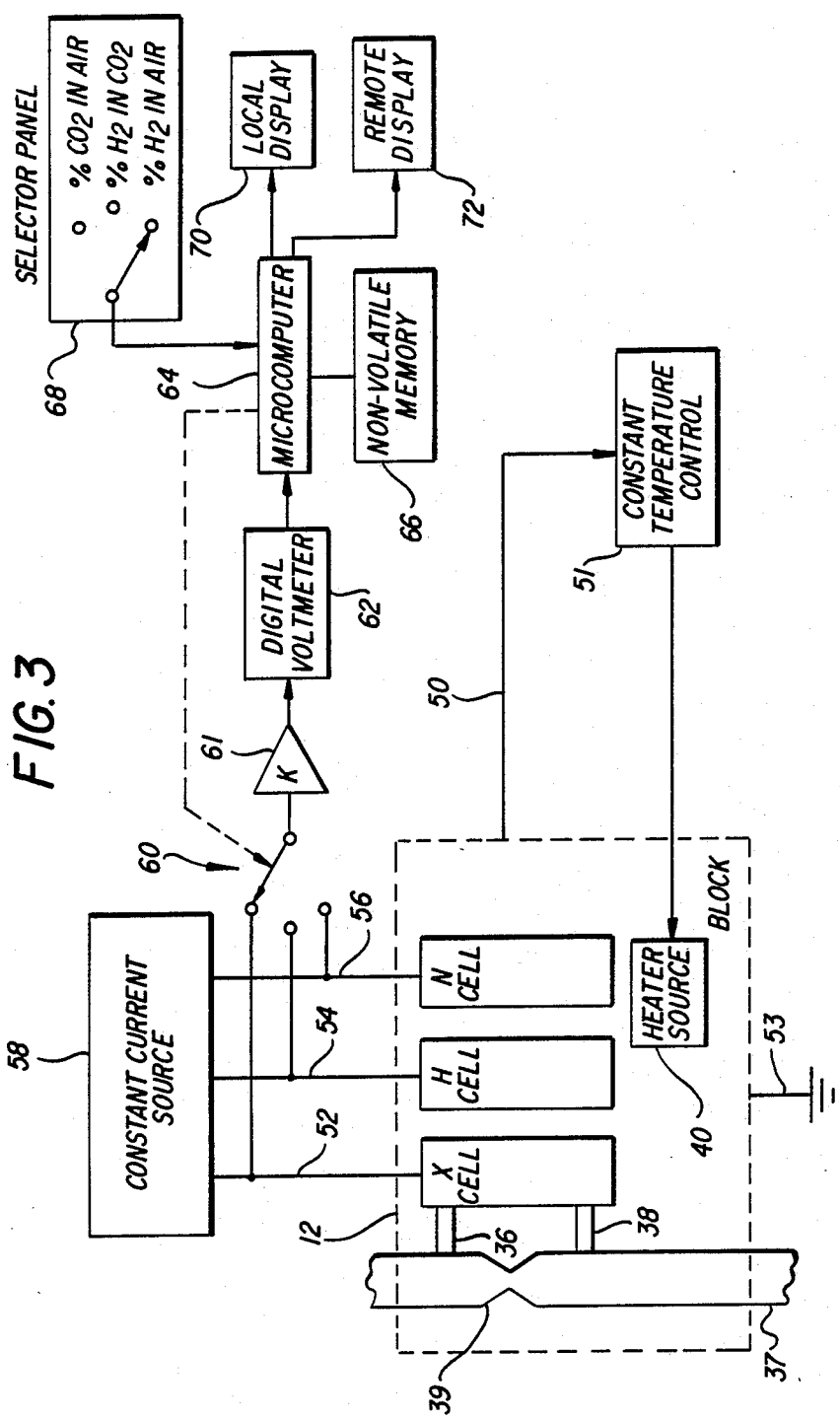
FIG. 3 is a schematic illustration of the analyzer instrument of the present invention utilizing the measurement cell block of FIG. 2.

FIG. 3 is a general block diagram of the present invention. The thermistors within X CELL, H CELL and N CELL are electrically connected via isolated leads 22 (FIG. 1) and leads 52, 54 and 56, respectively, to a constant current source 58. Leads 20 (FIG. 1) from the thermistors are electrically connected to block 12, which is grounded 53. As one nonlimiting example, a constant current of approximately 13 milliamps is supplied by constant current source 58 to each cell thermistor. As noted above, heat source 40 embedded within block 12 is regulated by a constant temperature control 51. Control 51 receives temperature feedback information from a sensor (not shown) embedded within block 12 via line 50.

A selector switch 60 is employed to sequentially connect a digital voltmeter (D.V.M.) 62 across each thermistor within X CELL, H CELL and N CELL. For the specific thermistors referenced above, a constant current in the range of 13 milliamps produces voltage drops across the thermistors in the range of 3.5 volts (for 100% carbon dioxide) to 6.0 volts (for 100% hydrogen) (see FIG. 6). Voltage readings are slightly scaled by an amplifier 61 to match the characteristics of digital voltmeter 62. Voltage readings across the X CELL, H CELL and N CELL thermistors are periodically sampled and sequentially fed to a microcomputer 64. Software, discussed below, within microcomputer 64 controls the measurement cycle wherein switch 60 is sequentially connected across X CELL, H CELL and N CELL thermistors. Initial calibration readings utilized in software calculations are stored in nonvolatile memory 66. A selector panel 68 provides means for manually inputting to microcomputer 64 the particular binary gas mixture measuring range under evaluation. As shown, selector panel 68 requires the operator to define for microcomputer 64 whether the mixture under analysis comprises "% $CO_2$ in air", "% $H_2$ in $CO_2$", or "% $H_2$ in air". A local display 70, i.e., at the analyzer instrument, and a remote display 72, e.g., within a central control room, provide the operator with a three digit readout on the percent composition of the binary gas mixture constituents. The third digit is intended primarily to indicate in which direction percent changes are occurring, and is not to absolute accuracy.

Figure 4:
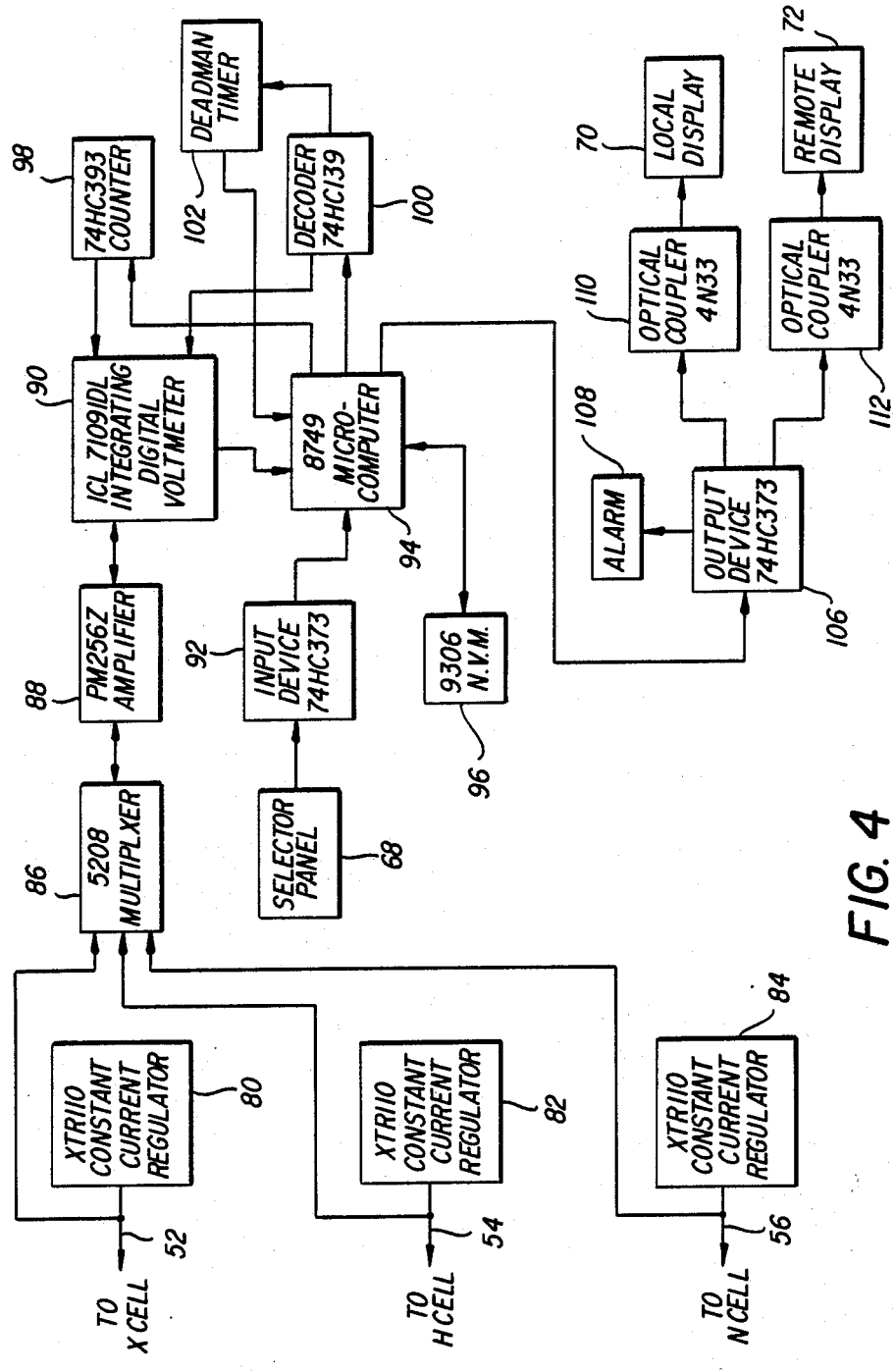
FIG. 4 is a more detailed block diagram implementation of several components represented in FIG. 3.

One detailed circuit board implementation of constant current source 58, selector 60, amplifier 61, digital voltmeter 62, microcomputer 64, nonvolatile memory 66, selector panel 68, local display 70 and remote display 72 is provided in block diagram form in FIG. 4. Those skilled in the art will recognize that other, equally acceptable implementations of the invention are possible.

Each X CELL, H CELL and N CELL thermistor is electrically connected, via leads 52, 54 and 56, respectively, to its own constant current regulator 80, 82 and 84, respectively. Constant current regulators 80, 82 and 84 each comprise a Burr-Brown XTR110 chip which provides all the elements required to hold the current constant within the thermistors at 13 or 14 milliamps within ±0.2 percent.

Connected to the output of constant current regulators 80, 82, and 84, and therefore the cell thermistors, is an analog multiplexer, type 5208, which sequentially samples the voltages across each thermistor. A two bit selecting address is supplied by the microcomputer in a pattern that preferably accesses four readings from each cell for averaging, thereby increasing instrument accuracy. Buffer amplifier 88, type PM256Z, provides very high impedence loading so that the on resistance of analog multiplexer 86 does not introduce an error into the calculations. Voltmeter 62 (FIG. 3) is implemented by an Intersil ICL 7109 integrating digital voltmeter chip, which is a significant element in the operation of the present invention. Chip 90 is an integrating dual slope zero correcting type with 12 bit digital output compatible with commercially available microcomputer hardware.

An input device chip 92 type 74HC373, provides a single chip micrcomputer 94, discussed below, with manually switched input information from selector panel 68 (FIG. 3). As noted above, panel 68 includes three switches which define the range of the binary gas mixture presently under evaluation, information which the software requires to calculate a correct constituent gas compositional percentage. Preferably, the selector panel also contains a switch for defining which of two cell blocks is presently in use. Two cell blocks are desirable for reasons of security, that is, monitoring procedures could continue notwithstanding that a defect develops in one of the blocks, e.g., a reference gas unexpectedly dissipates from a cell resulting in incorrect voltage readings. Different cell blocks produce slightly different calibration measurements which for improved accuracy must each be saved in nonvolatile memory for later recovery and use in percent calculations.

As described below, the selector panel further includes a calibrate switch and three calibration switches, one for each of the three gases encountered, i.e., hydrogen, carbon dioxide and air. Each calibration switch operates a solenoid valve which pipes one of the known gases into the measurement cell, X CELL, for a field check of instrument accuracy. Also, several additional switches are connected directly to microcomputer 94 via an options dip switch (e.g., "Standard", "Calibrate D.V.M.", and "Logout"). These switches are discussed below with reference to FIGS. 5A and 5B.

The heart of the analyzer instrument comprises a microcomputer chip 94, e.g., an Intel 8749. This chip includes 2K of ROM program storage and 64 bytes of RAM memory for storage of variables, working registers and stack save. Nonvolatile memory chip 96, type 9306, contains the calibration standards for each of the two cell blocks. At power reset, the appropriate calibration standards are read into RAM for use in calculating percent concentration. Data transfer is serial with the software generating the required sequence of clock and data.

Additional system components include a counter 98, type 74HC393, which provides clock means from micrcomputer chip 94 to digital voltmeter 90, and a decoder chip 100, type 74HC139, which is connected between micrcomputer 94 and digital voltmeter 90, and which also provides output to a deadman timer 102. Timer 102 is a safety device which will automatically reset the micrcomputer should normal activity be disrupted, e.g., as a result of a power disturbance. Micrcomputer chip 94 provides output via device 106, type 74HC373, to an alarm 108 and identical optical couplers 110 and 112, type 4N33. Alarm 108 provides a warning indication should the percent hydrogen in air mixture reach the potentially explosive value of 85%. Optocouplers 110 and 112 drive local display 70 and remote display 72, respectively.

Figure 5A:
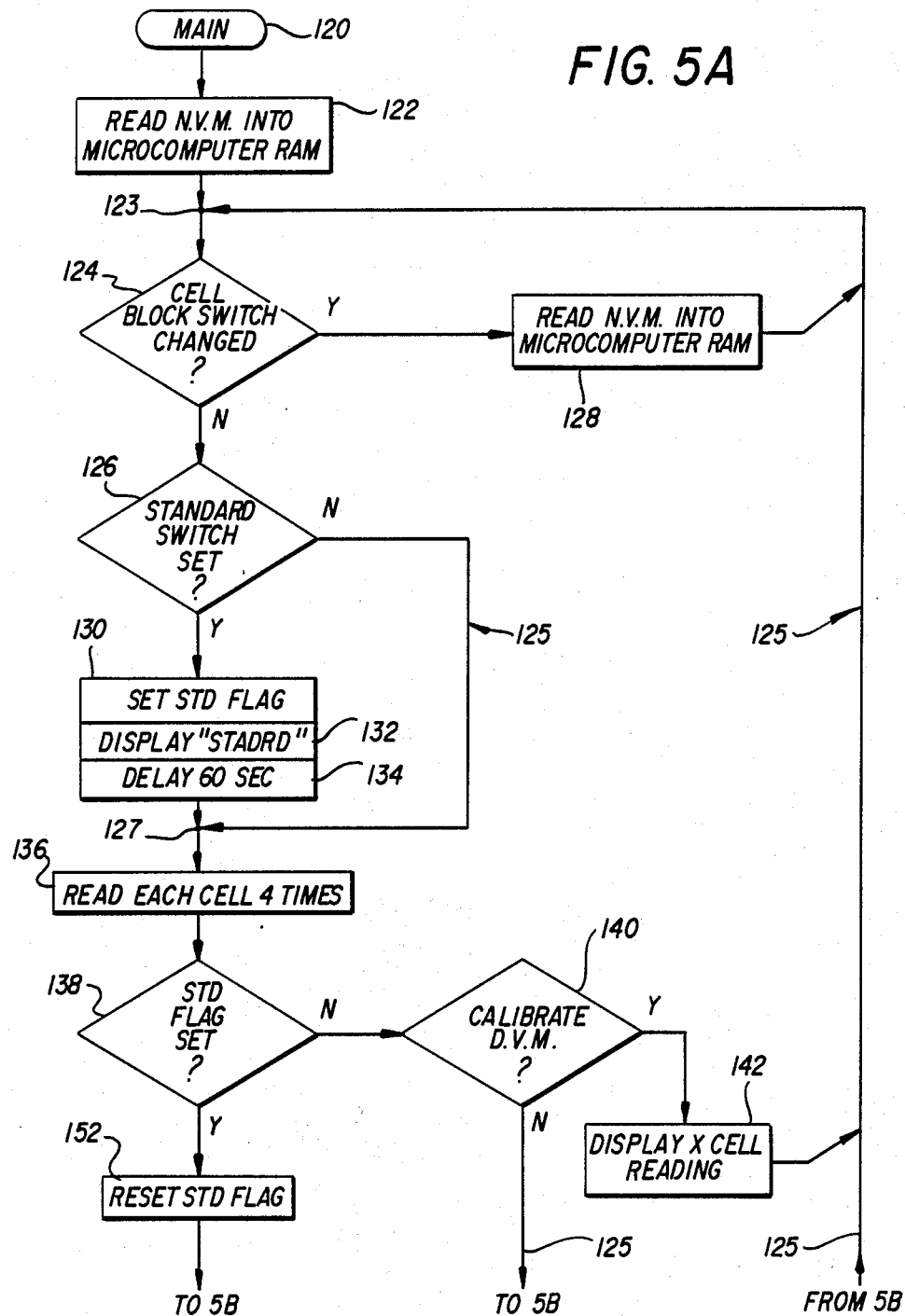
FIGS. 5A and 5B depict a flowchart of one embodiment of control software utilized in the present invention.
Figure 5B:
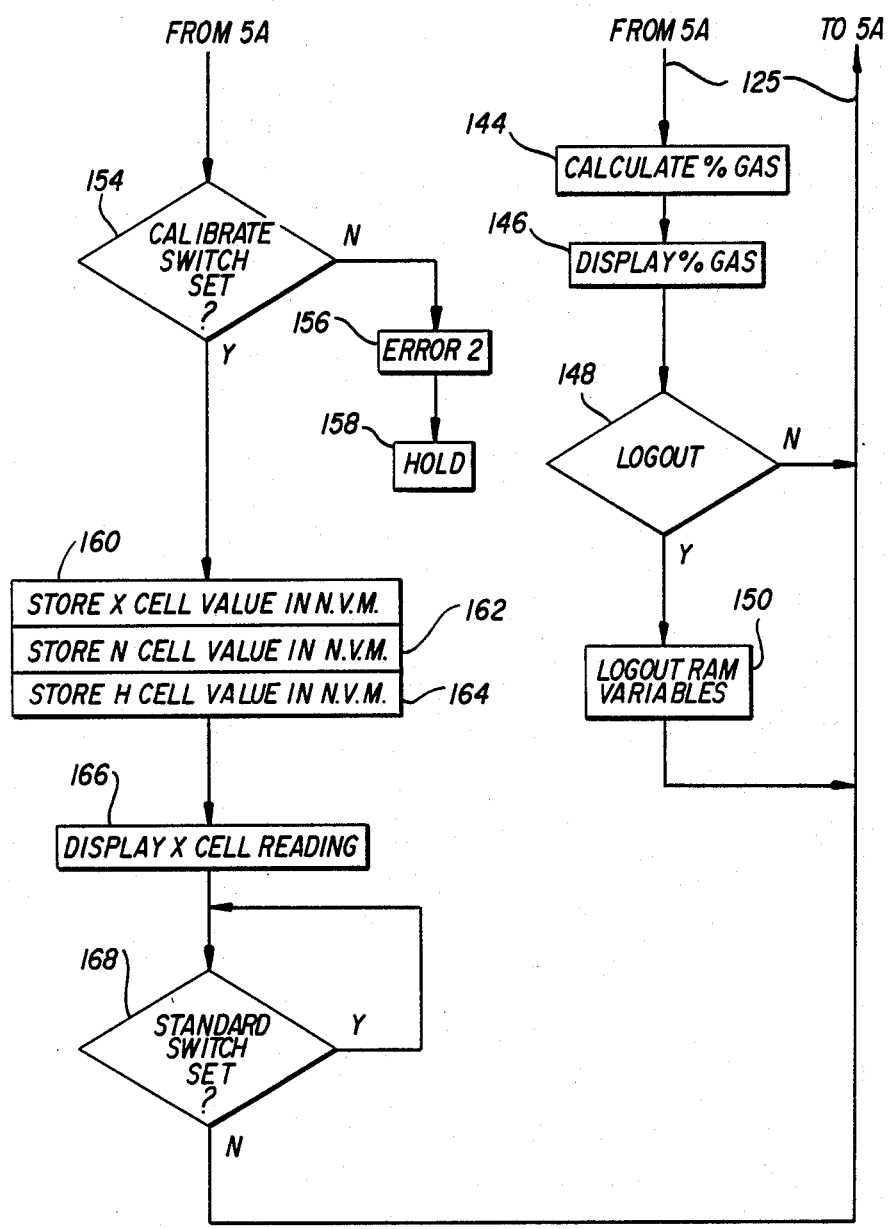

A software overview will now be provided with reference to the flowchart of FIGS. 5A and 5B.

Referring first to FIG. 5A, the controller enters the main loop at 120 "Main", and proceeds to instruction 122 "Read N.V.M. Into Microcomputer RAM", which directs initialization of system values following power off reset or first time powering of the instrument. From instruction 122 the controller is directed to junction 123 where it enters the normal processing loop 125, indicated by the bold line in FIGS. 5A and 5B. During normal operation, all switches on the options dip switch remain "off" and all selector panel switches experience no change. Briefly explained, in one pass through normal loop 125: (1) the voltage across each cell thermistor is taken four times, for averaging and increased accuracy; (2) the percent gas concentration is calculated from the read voltages and the stored calibration standards; and (3) the percent concentration is displayed at local display 70 and remote display 72.

Once in normal loop 125, the controller proceeds from junction 123 to inquiry 124 "Cell Block Switch Changed?" where the controller determines whether the operator has manually switched from one cell block to the other block, e.g., for repair of the first block. If the cell block switch setting has changed, then the controller deviates from normal loop 125, passing to instruction 128 "Read N.V.M. Into Microcomputer RAM", which directs that standard calibration readings for the new cell block be brought into RAM. As noted above, since different cell blocks do not respond exactly alike, e.g., because thermistors are manufactured only within certain tolerances, standard calibration readings for each cell block are initially taken and separately stored in nonvolatile memory for subsequent recall and use in the calculations described below. From instruction 128 flow is back to junction 123 of normal loop 125.

After inquiry 124, the controller is directed to determine whether the standard switch has been set, "Standard Switch Set?" 126. Standard calibration of cell values for storage in nonvolatile memory (i.e., HCALIB, NCALIB, CCALIB, NSTD and HSTD, described below) will preferably be performed at time of instrument construction. However, in certain cases, such as repair of an instrument component which may effect the analog portion of the circuit (e.g., replacement of a cell thermistor) standard calibration values may be obtained and read into nonvolatile memory on-site. Normally the Standard Switch is "off" and the controller is directed from inquiry 126 to junction 127, and hence to instruction 136 "Read Each Cell 4 Times" where it measures the voltage across each cell thermistor four times. Greater instrument accuracy is obtained by averaging multiple readings, e.g., four, six or eight readings. Also, improved accuracy is believed possible by sequentially reading the voltage across each thermistor as a cycle, and then repeating the cycle four times to obtain the desired number of readings.

After reading each thermistor four times, the controller determines whether the "STD" flag has been set, "STD Flag Set?" 138. STD Flag is set only when the operator flips the Standard Switch "on", meaning cell readings are to be collected for storage in nonvolatile memory as standard calibrations. Continuing within normal loop 125, flow is to inquiry 140 "Calibrate D.V.M.?", which is a check to determine whether the operator wishes to adjust instrument accuracy by introducing a 100% known gas into X CELL. If the Calibrate D.V.M. dip switch is set, the controller proceeds to instruction 142 "Display X CELL Reading", which provides the operator with visual feedback for manual scaling adjustment of the digital voltmeter 62 (FIG. 3). Again, a "yes" to either inquiry 138 or inquiry 140 directs the controller outside normal loop 125.

Referring now to FIG. 5B, in normal operation the controller is next directed to calculate the percent composition of the binary gas mixture under evaluation "Calculate % Gas" 144. Five standards are initially calibrated, as described below, and stored in nonvolatile memory for later use in calculating percent composition readings. These standards are:

NSTD = N CELL standard reading;
HSTD = H CELL helium standard reading;
NCALIB = X CELL nitrogen calibration reading;
HCALIB = X CELL hydrogen calibration reading; and
CCALIB = X CELL carbon dioxide calibration reading.

Specific, preferred formulas for calculating percent gas composition for each of the three binary mixtures typically experienced in turbo generation are as follows:

% HYDROGEN IN AIR calculation: (1)

$$\frac{[(READX - READN) + (NSTD - NCALIB)]}{(READH - READN)} \times \frac{(HSTD - NSTD)}{(HCALIB - NCALIB)} \times 1000$$

% HYDROGEN IN CO$_2$ calculation: (2)

$$\frac{[(READX - READN) + (NSTD - CCALIB)]}{(READH - READN)} \times \frac{(HSTD - NSTD)}{(HCALIB - CCALIB)} \times 1000$$

% CO$_2$ IN AIR calculation: (3)

$$\frac{[(READN - READX) + (NCALIB - NSTD)]}{(READH - READN)} \times \frac{(HSTD - NSTD)}{(NCALIB - CCALIB)} \times 1000$$

wherein:
READN = present N CELL reading;
READH = present H CELL reading; and
READX = present X CELL reading of binary mixture.

The appropriate formula is selected by the operator through the binary gas mixture setting on the instrument's selector panel. During normal operation, only the % HYDROGEN IN AIR formula is used to calculate percent gas composition. Formulas (1), (2) and (3) each include a correction for measurement cell block temperature change from that temperature at which calibration standards were obtained. Those skilled in the art will recognize that the formulas (1), (2) and (3) can be rewritten for any binary gas mixture under evaluation.

From instruction 144, flow proceeds to instruction 146 "Display % Gas", where the controller outputs the calculated composition percentage to the local and remote displays. Display is preferably to three decimal digits, or 99.9 percent, which is the reason for the constant 1000 in formulas (1), (2) and (3). Normally, minor errors slightly negative near zero or over 100 will be clamped for a more realistic display. This clamp would be removed if the Calibrate Switch was "on" to permit an accuracy check.

Subsequent output of the percent composition reading, the controller continues to inquiry 148 "Logout?" which typically is answered "no", and hence to junction 123 to repeat loop 125.

Logout is a special feature which can be added as an aid to debugging possible trouble within the instrument and to assisting in efforts to increase the instrument's accuracy. If the Logout Switch is set "yes" then the controller proceeds to "Logout RAM Variables" 150. During normal loop cycling, microcomputer RAM will contain the data used to calculate percent gas concentration to be displayed, e.g., READN, READH, READX, NSTD, HSTD, HCALIB, NCALIB and CCALIB. Activation of the Logout Switch initiates a logout series for either presentation to the display for manual recordation of values, or to a printing device, i.e., if connected to the system. If values are to be manually recorded, a logout delay is incorporated into the display of each variable. Preferably, the normally calculated percent composition is also logged out so a manual calculation using the RAM variables can be conducted to check internal calculations. Also, each logout will include the minimum and maximum READH and READN values as a monitor on long term block temperature.

Returning to FIG. 5A, the controller exits normal loop 125 at inquiry 126 if the operator has set the Standard Switch "on", meaning that read values are to be stored as calibration standards in nonvolatile memory for future reference. If "on", flow proceeds to direction 130 "Set STD Flag" and hence to instruction 132 "Display STADRD". STADRD is displayed as visual feedback to the operator that the instrument is functioning properly by acknowledging the Standard Switch setting. After instruction 132, the controller delays action for 60 seconds "Delay 60 Sec" 134 to allow the operator time to purge and fill the X CELL with a known gas. Cell readings are then taken four times 136 "Read Each Cell 4 Times". If the STD Flag is set, the controller is directed from inquiry 138 "STD Flag Set?" to instruction 152 "Reset STD Flag" and hence to inquiry 154 "Calibrate Switch Set?" (see FIG. 5B). Inquiry 154 is simply a software double check against possible human error in that for standard calibration readings to be stored in nonvolatile memory, both the Standard Switch and the Calibration Switch must be set. If the Calibration Switch is "off", the controller is directed to instruction 156 "Display ERROR" and hence to hold operations, "HOLD" 58. At this point, the operator must recheck his switch settings to uncover the source of the error, and reset the computer, whereupon the controller reenters the software at "Main" 120.

Figure 6:
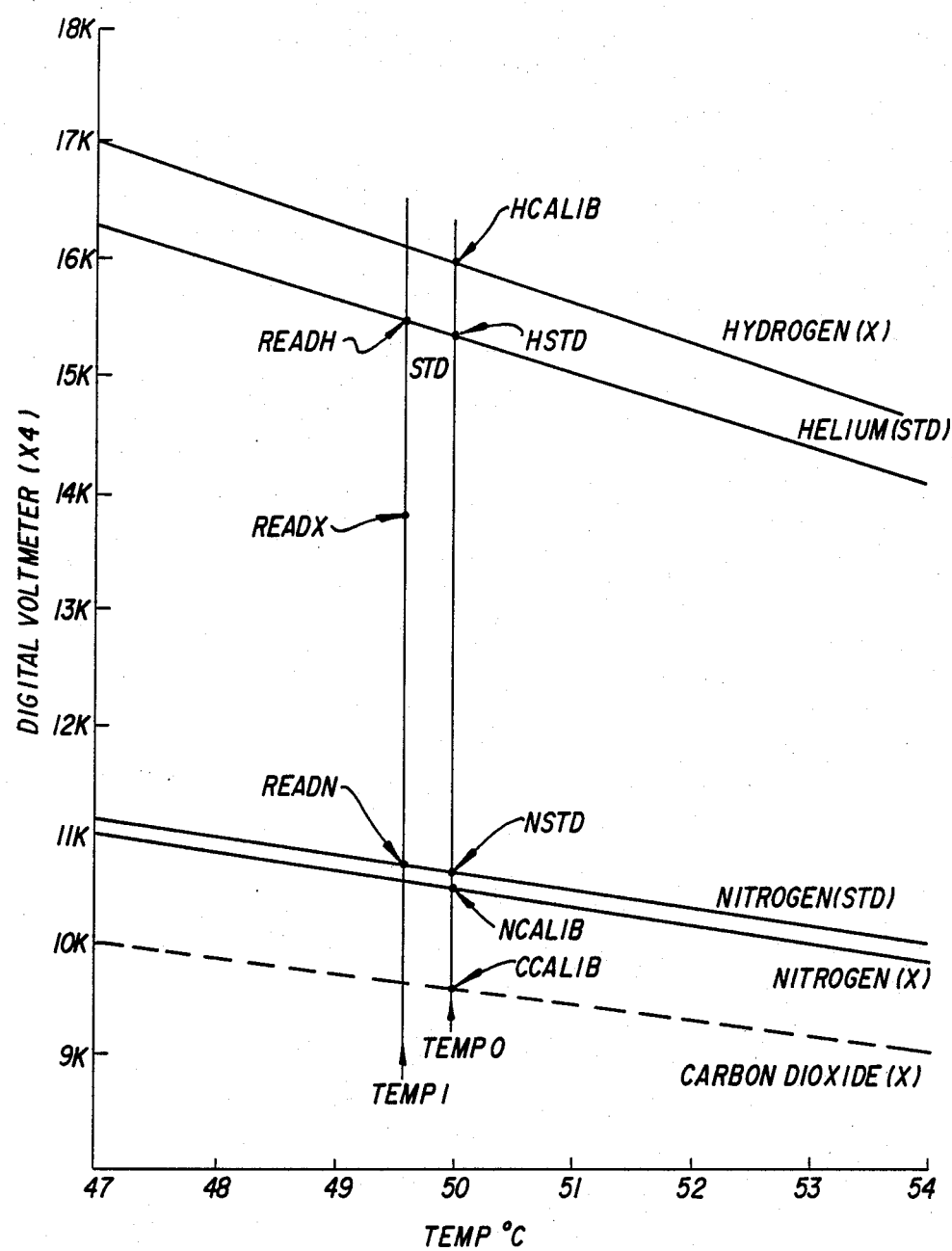
FIG. 6 is a graphic illustration of the change in voltage across cell thermistors as a function of temperature for hydrogen, nitrogen and carbon dioxide gases.

Assuming the Calibrate Switch is set, the controller proceeds to instructions 160, 162 and 164 to "Store X CELL Value In N.V.M.", "Store N CELL Value In N.V.M.", and "Store H CELL Value In N.V.M.", respectively. Since several minutes are required to calibrate each gas, i.e., hydrogen, nitrogen and carbon dioxide, a slight correction may be desirable depending upon the temperature change from the previous calibration of a standard. FIG. 6 graphically illustrates how calibration standards, i.e., HSTD, NSTD, HCALIB, NCALIB and CCALIB, change with temperature about a substantially constant block temperature of 50° Celsius. FIG. 6, constructed from empirical data, is a plot of digital voltmeter readings for the given gases versus temperature. Correction of voltage readings as a function of temperature can be easily accomplished using READH, READN, HSTD and NSTD readings and simple proportional arithmetic. Also, greater accuracy in the resultant calculations is believed obtainable by serially storing calibration standards, HSTD, NSTD, HCALIB, NCALIB, and CCALIB, with the least important gas stored first and the most important last. Thus, a preferred order of calibration for turbo generation monitoring is to sequentially store CCALIB, NCALIB and then HCALIB. The last N CELL and H CELL values are those ultimately stored in nonvolatile memory as NSTD and HSTD, respectively.

One procedure for recording calibration standards comprises:

allow instrument to reach stabilization temperature;

introduce a known 100% carbon dioxide gas into the measurement cell;

measure and store the voltage across X CELL thermistor as carbon dioxide calibration standard reading (CCALIB);

introduce a known 100% nitrogen gas into the measurement cell;

measure and store the voltage across X CELL thermistor as the nitrogen calibration standard reading (NCALIB);

introduce a known 100% hydrogen gas into the measurement cell; and measure and store the voltage across the X CELL thermistor as the hydrogen calibration standard reading (HCALIB);

Further, as noted above, the voltage drops across the N Cell and H Cell thermistors are automatically measured and stored as NSTD and HSTD, respectively, with the recordation of a calibration standard.

Returning to the flowchart, from instruction 164, the controller is directed to display the X CELL thermistor reading, "Display X CELL Reading" 166, which is simply visual feedback for the operator that an appropriate value is being read and stored into nonvolatile memory as CCALIB, NCALIB or HCALIB. Thereafter the controller is directed at inquiry 168 "Standard Switch Set?" to again check the Standard Switch setting, this time to verify that the operator has switched "off" the Standard Switch after the calibration standard has been recorded. Once confirmed, the controller returns to normal operating loop 125 via junction 123.

Finally, as noted above, typical D.M.V. readings as a function of block temperature for READH, READX, READN, HSTD, NSTD, HCALIB, NCALIB and CCALIB for the specific instrument embodiment discussed herein are illustrated in FIG. 6. As shown, HSTD and NSTD are near opposite ends of the range of possible voltage readings (defined by HCALIB and NCALIB) for a hydrogen and air binary mixture.

Although one embodiment of the analyzer instrument and analysis method of this invention has been described in the foregoing detailed description, it will be understood that the invention is not limited to the particular embodiment discussed herein but is capable of numerous rearrangements, modifications and substitutions without departing from the scope of the invention. For example, if desired, more than two reference cells may be utilized to increase accuracy if two or more different binary gas mixtures are to be analyzed. Other changes will suggest themselves to those skilled in the art. The following claims are intended to encompass all such modifications.

What is claimed is:

1. A gas analyzer instrument capable of determining the percent composition of a binary gas mixture of known constituents, said analyzer instrument comprising:
   a first reference cell having a first gas therein, said first gas having a thermal conductivity near the thermal conductivity of one of said constituent gases;
   a measurement cell having said binary gas mixture therein;
   means for maintaining said cells at a substantially constant temperature;
   a thermistor positioned within each of said cells;
   means for supplying a substantially constant electrical current to each of said thermistors for heating thereof, the gas in each of said cells conducting heat away from the thermistor;
   voltage measuring means selectably connectable across each of said thermistors to measure voltage drop across said thermistors; and
   computational means for automatically translating the voltage drop across said measurement cell thermistor into a percent compositional reading of said binary gas constituents, said computational means utilizing the voltage drop across said first cell thermistor as a reference.

2. The analyzer instrument of claim 1, further comprising:
   a second reference cell having a second gas therein, said second gas having a thermal conductivity near the thermal conductivity of the other of said constituent gases; and
   wherein the computational means automatically translates the voltage drop across said measurement cell thermistor into a percent compositional reading of said binary gas constituents utilizing the voltage drop across at least one of said first and second cell thermistors as a reference.

3. The analyzer instrument of claim 2, wherein said instrument is capable of being used to determine percent composition of the constituents within each of a plurality of different known binary gas mixtures.

4. The analyzer instrument of claim 3, further comprising at least three reference cells, each of said reference cells having a gas therein with a thermal conductivity near the thermal conductivity of a constituent gas in one of said plurality of mixtures.

5. The analyzer instrument of claim 3, further comprising means for displaying the percent compositional reading of said binary gas constituents.

6. The analyzer instrument of claim 5, wherein said display means includes a plurality of selectable display scales, the appropriate display scale being manually selected based upon of the binary gas mixture under analysis.

7. The analyzer instrument of claim 2, wherein said first gas is sealed in said first reference cell and said second gas is sealed in said second reference cell.

8. The analyzer instrument of claim 2, wherein said first gas comprises one of said constituent gases.

9. The analyzer instrument of claim 8, wherein said second gas comprises the other of said constituent gases.

10. The analyzer instrument of claim 2, further comprising a substantially solid block within which said cells are located, said block being manufactured of metal.

11. The analyzer instrument of claim 10, wherein said temperature maintaining means maintains said block at a substantially constant temperature.

12. The analyzer instrument of claim 11, wherein said cells are arranged in a triangular shaped configuration within said block.

13. The analyzer instrument of claim 12, wherein said maintaining means includes heating means positioned substantially central said triangular shaped configuration of cells.

14. The analyzer instrument of claim 11, wherein said substantially constant block temperature is above standard room temperature.

15. The analyzer instrument of claim 13, wherein said substantially constant block temperature is approximately 50 degrees Celsius.

16. The analyzer instrument of claim 13, wherein said thermistors comprise negative temperature coefficient of resistivity thermistors.

17. The analyzer instrument of claim 3, wherein said instrument is used for monitoring a hydrogen gas cooled turbine driven electrical generator, and wherein said first gas comprises helium and said second gas comprises nitrogen.

18. The analyzer instrument of claim 17, wherein said instrument is capable of being used to determine percent composition of the constituents within each of three different binary gas mixtures, said different mixtures comprising carbon dioxide and air, hydrogen and carbon dioxide, and hydrogen and air.

19. The analzyer instrument of claim 18, further comprising alarm means for providing an indication when the percent composition of said hydrogen and air mixture is at a dangerous level.

20. The analyzer instrument of claim 18, wherein said measurement cell includes a gas inlet for continuously introducing a binary gas mixture of unknown percent composition from said electrical generator into said measurement cell and a gas outlet for continuously exhausting said gas mixture.

21. The analyzer instrument of claim 18 further comprising:
   means for calculating and storing standard nitrogen reference cell and standard helium reference cell readings;
   means for calibrating nitrogen gas in said measurement cell and for storing said nitrogen calibration reading in memory;
   means for calibrating hydrogen gas in said measurement cell and for storing said hydrogen calibration reading in memory; and
   means for calibrating carbon dioxide in said measurement cell and for storing said carbon dioxide calibration reading in memory.

22. The analyzer instrument of claim 21, wherein said computational means utilizes said stored nitrogen and helium reference standard readings and said stored nitrogen, hydrogen and carbon dioxide calibration readings in translating the voltage drop across said measurement cell thermistor into a percent compositional reading of said binary gas constituents.

23. The analyzer instrument of claim 22, wherein said percent hydrogen in air composition is calculated from:

$$\frac{[(READX - READN) + (NSTD - NCALIB)]}{(READH - READN)} \times$$

-continued $$\frac{(HSTD - NSTD)}{(HCALIB - NCALIB)} \times 1000$$

wherein:
- READN = present nitrogen cell reading
- READH = present helium cell reading
- READX = present measurement cell reading
- NSTD = nitrogen standard reading from memory
- HSTD = helium standard reading from memory
- NCALIB = nitrogen calibration reading from memory
- HCALIB = hydrogen calibration reading from memory
- CCALIB = carbon dioxide calibration reading from memory.

24. The analyzer instrument of claim 23, wherein said percent hydrogen in carbon dioxide composition is calculated from:

$$\frac{[(READX - READN) + (NSTD - CCALIB)]}{(READH - READN)} \times$$

$$\frac{(HSTD - NSTD)}{(HCALIB - CCALIB)} \times 1000$$

25. The analyzer instrument of claim 24, wherein said percent carbon dioxide in air composition is calculated from:

$$\frac{[(READN - READX) + (NCALIB - NSTD)]}{(READH - READN)} \times$$

$$\frac{(HSTD - NSTD)}{(NCALIB - CCALIB)} \times 1000$$

26. The analyzer instrument of claim 25, wherein said NSTD, HSTD, NCALIB, HCALIB and CCALIB readings are stored in nonvolatile memory.

27. A percent composition determining instrument for use with a binary gas mixture of known constituents, said instrument comprising in combination:
- a block;
- means for maintaining said block at a substantially constant temperature;
- a plurality of gas cells positioned within said block;
- some of said gas cells comprising sealed reference chambers with known gases therein;
- means for introducing the binary gas mixture into one of said cells;
- a thermistor within each of said cells;
- means for supplying a substantially constant electrical current to each of said thermistors for heating thereof, the gas in each of said cells conducting heat away from said thermistor;
- voltage measuring means selectably connectable across each of said cells to measure voltage drop across said thermistors; and
- computational means for automatically correlating the voltage drop across the thermistor within said cell containing the binary gas mixture with a percent compositional reading of said binary gas constituents, said computational means utilizing the voltage drop across the thermistor within at least one of said sealed chambers as a reference.

28. The instrument of claim 27, wherein said instrument is capable of being used to determine percent composition of the constituents within each of a plurality of different binary gas mixtures.

29. The instrument of claim 27, wherein said block is substantially solid and manufactured of metal.

30. The analyzer instrument of claim 29, wherein said temperature maintaining means maintains said block at a substantially constant temperature.

31. The instrument of claim 30, wherein said substantially constant block temperature is approximately 50 degrees Celsius.

32. The instrument of claim 27, wherein said thermistors comprise negative temperature coefficient of resistivity thermistors.

33. A method for determining the percent composition of a gas mixture of two known constituents, said method comprising the steps of:
- (A) providing a first reference cell having a first gas and a thermistor sealed therein, said first gas having a thermal conductivity near the thermal conductivity of one of said two constituent gases;
- (B) providing a second reference cell having a second gas and a thermistor sealed therein, said second gas having a thermal conductivity near the thermal conductivity of the other of said two constituent gases;
- (C) providing a measurement cell and a thermistor therein;
- (D) introducing said binary gas mixture into said measurement cell;
- (E) maintaining said cells at a substantially constant temperature;
- (F) supplying a substantially constant electric current to each of said thermistors for heating thereof, the gas in each of said cells conducting heat away from the thermistor;
- (G) measuring the voltage drop across each of said thermistors; and
- (H) correlating the voltage drop across said measurement cell thermistor with a percent compositional reading of said binary gas mixture constituents, said correlation step utilizing the voltage drop across at least one of said first and second cell thermistors as a reference.

34. The method of claim 33, wherein said method is capable of being used to determine percent composition of the constituents within each of a plurality of different binary gas mixtures, and wherein said providing step (A) includes providing a first gas having a thermal conductivity near the thermal conductivity of a constituent gas in one of said plurality of mixtures, and said providing step (B) includes providing a second gas having a thermal conductivity near the thermal conductivity of another constituent gas in one of said plurality of mixtures.

35. The method of claim 34, further comprising displaying the percent compositional reading of said binary gas constituents.

36. The method of claim 35, further comprising manually selecting a display scale from one of a plurality of scales based upon the binary gas mixture under analysis.

37. The method of claim 34, wherein said temperature maintaining step (E) includes maintaining said cells at approximately 50 degrees Celsius.

38. The method of claim 34, wherein said method is capable of being used to determine percent composition of the constituents within each of three different binary gas mixtures, said different mixtures comprising carbon dioxide and air, hydrogen and carbon dioxide, and hydrogen and air.

39. The method of claim 38 further comprising initially calibrating said cells.

40. The method of claim 39 wherein said method is used for monitoring a hydrogen gas cooled electrical generator, and wherein said first gas provided in step (A) comprises helium and said second gas provided in step (B) comprises nitrogen.

41. The method of claim 40, wherein said calibration step includes:
  calculating and storing standard nitrogen reference cell and helium reference cell readings;
  calibrating nitrogen gas in said measurement cell and storing said nitrogen calibration reading in memory;
  calibrating hydrogen gas in said measurement cell and storing said hydrogen calibration reading in memory; and
  calibrating carbon dioxide in said measurement cell and storing said carbon dioxide calibration reading in memory.

42. The method of claim 41, wherein said correlating step (H) includes calculating the hydrogen in air gas composition from:

$$\frac{[(READX - READN) + (NSTD - NCALIB)]}{(READH - READN)} \times$$

$$\frac{(HSTD - NSTD)}{(HCALIB - NCALIB)} \times 1000$$

wherein:

READN = present nitrogen cell reading
READH = present helium cell reading
READX = present measurement cell reading
NSTD = nitrogen standard reading from memory
HSTD = helium standard reading from memory
NCALIB = nitrogen calibration reading from memory
HCALIB = hydrogen calibration reading from memory
CCALIB = carbon dioxide calibration reading from memory.

43. The method of claim 42, wherein said correlating step includes calculating the percent hydrogen in carbon dioxide composition from:

$$\frac{[(READX - READN) + (NSTD - CCALIB)]}{(READH - READN)} \times$$

$$\frac{(HSTD - NSTD)}{(HCALIB - CCALIB)} \times 1000$$

44. The method of claim 43, wherein said correlating step includes calculating the percent carbon dioxide in air from:

$$\frac{[(READN - READX) + (NCALIB - NSTD)]}{(READH - READN)} \times$$

$$\frac{(HSTD - NSTD)}{(NCALIB - CCALIB)} \times 1000$$

45. The method of claim 44, further comprising initially storing said NSTD, HSTD, NCALIB, HCALIB and CCALIB readings in nonvolatile memory.

* * * * *